(12) United States Patent
Merriman et al.

(10) Patent No.: US 11,597,971 B2
(45) Date of Patent: Mar. 7, 2023

(54) METHODS FOR ANALYSIS OF DNA FRAGMENTS (71) Applicant: LIFE TECHNOLOGIES CORPORATION, Carlsbad, CA (US)

(72) Inventors: Barry Merriman, Encinitas, CA (US); Paul Mola, San Diego, CA (US); Mark Gardner, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1008 days.

(21) Appl. No.: 14/528,242

(22) Filed: Oct. 30, 2014

(65) Prior Publication Data
US 2015/0057182 A1    Feb. 26, 2015

Related U.S. Application Data (63) Continuation of application No. PCT/US2013/031515, filed on Mar. 14, 2013.

(60) Provisional application No. 61/640,793, filed on May 1, 2012.

(51) Int. Cl.
*C12Q 1/6874* (2018.01)
(52) U.S. Cl.
CPC ................. *C12Q 1/6874* (2013.01)
(58) Field of Classification Search
None
See application file for complete search history.

(56) References Cited

U.S. PATENT DOCUMENTS

2010/0035252 A1    2/2010    Rothberg et al.

FOREIGN PATENT DOCUMENTS

WO    2012/045889    4/2012

OTHER PUBLICATIONS

Sakata et al. DNA Sequencing Using Genetic Field Effect Transistor, The 13th International Confrrence on Solid-State Sensors. Actuators and Microsystems, Seoul, Korea, Jun. 5-9, 2005.*
Grondin, R. et al., "Six-month partial suppression of Huntingtin is well tolerated in the adult rhesus striatum", *Occasional Paper, Brain A Journal of Neurology*, vol. 135, 2012, pp. 1197-1209.
Law, H. et al., "Trinucleotide Repeat Analysis of Huntington's Disease gene in Singapore", *Annals Academy of Medicine*, vol. 30, No 2., Mar. 2001, pp. 122-127.

* cited by examiner

*Primary Examiner* — Joseph Woitach (57) ABSTRACT

A method of genotyping includes applying a sample solution including a plurality of copies of a sample polynucleotide to an array of sensors. The sample polynucleotide includes a region associated with an allele. The method further includes measuring using a plurality of sensors of the array of sensors a characteristic of the region of the plurality of copies of the sample polynucleotide and determining using a computational circuitry and the measured characteristics a statistical value indicative of the allele.

7 Claims, 7 Drawing Sheets

Specification includes a Sequence Listing.

HUNTINGTON'S DISEASE: CAG REPEAT IN HTT GENE

| REPEAT COUNT | CLASSIFICATION | DISEASE STATUS |
| --- | --- | --- |
| <27 | NORMAL | UNAFFECTED |
| 27-35 | INTERMEDIATE | UNAFFECTED |
| 36-39 | VARIABLE PENETRANCE | +/- AFFECTED |
| >39 | FULL PENETRANCE | AFFECTED |
| >60 | JUVENILE ONSET | AFFECTED |

NUMBER OF UNITS

SEQUENCE LISTING

```
<160> NUMBER OF SEQ ID NOS: 5

<210> SEQ ID NO 1
<211> LENGTH: 12
<212> TYPE: DNA
<213> ORGANISM: Homo sapiens

<400> SEQUENCE: 1
gatgatgatg at                                                          12

<210> SEQ ID NO 2
<211> LENGTH: 15
<212> TYPE: DNA
<213> ORGANISM: Homo sapiens

<400> SEQUENCE: 2
gaagaagaag aagaa                                                       15

<210> SEQ ID NO 3
<211> LENGTH: 15
<212> TYPE: DNA
<213> ORGANISM: Homo sapiens

<400> SEQUENCE: 3
gaagaagatg aagaa                                                       15
```

```
<210> SEQ ID NO 4
<211> LENGTH: 146
<212> TYPE: DNA
<213> ORGANISM: Homo sapiens

<400> SEQUENCE: 4
tcccaagctc ttcctcttcc ctagatcaat acagacagaa gacaggtgga tagatagata      60
gatagataga tagatagata gatagataga tatcattgaa agacaaaaca gagatggatg     120
atagatacat gcttacagat gcacac                                          146

<210> SEQ ID NO 5
<211> LENGTH: 88
<212> TYPE: DNA
<213> ORGANISM: Homo sapiens

<400> SEQUENCE: 5
tattccattg tatctatctg tctgtctgtc tatctatcta tctatctatc tatctatcta      60
tctatctatc tatctatcac agtttctt                                         88
```

METHODS FOR ANALYSIS OF DNA FRAGMENTS

CROSS-REFERENCE TO RELATED APPLICATION(S)

This application is a continuation of PCT Application No. PCT/US2013/031515, which claims benefit of U.S. Provisional Application No. 61/640,793, filed May 1, 2012, which are incorporated herein by reference in their entirety.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

FIELD OF THE DISCLOSURE

The present disclosure relates to the field of genetic analysis, for example, the field of polynucleotide (e.g., DNA) analysis for the purpose of, for example, human identification, or the identification within or between other species of plants, animals or other living organisms.

BACKGROUND

There has been increasing interest in using genetic markers for human identification (HID). Such identification is particularly useful in forensic applications, paternity testing, and inherited disease analysis. However, conventional methods, such as gel electrophoresis sizing, are time consuming and labor intensive.

As such, an improved method of detecting or analyzing genetic markers would be desirable.

SUMMARY

In a first aspect, a method of genotyping includes applying a sample solution including a plurality of copies of a sample polynucleotide to an array of sensors. The sample polynucleotide includes a region associated with an allele. The method further includes measuring using a plurality of sensors of the array of sensors a characteristic of the region of the plurality of copies of the sample polynucleotide and determining using a computational circuitry and the measured characteristics a statistical value indicative of the allele.

In a second aspect, a method of genotyping includes applying a sample solution including a plurality of copies of a sample polynucleotide to an array of sensors. The sample polynucleotide includes a variable number tandem repeat region associated with an allele. The method further includes sequencing with a plurality of sensors of the array of sensors at least the variable number tandem repeat region of the plurality of copies of the sample polynucleotide, determining with a computational circuitry a number of tandem repeats with the variable number tandem repeat region for a set of sequenced copies of the plurality of copies, and determining with the computational circuitry based at least in part on determining the number of tandem repeats a statistical value indicative of the allele.

In a third aspect, a method of genotyping includes amplifying a sample polynucleotide to provide a plurality of copies of the sample polynucleotide. The sample polynucleotide includes a variable number tandem repeat region associated with an allele associated with human identification. The method further includes applying a sample solution including the plurality of copies of a sample polynucleotide to an array of sensors, sequencing with a plurality of sensors of the array of sensors at least the variable number tandem repeat region of the plurality of copies of the sample polynucleotide, determining with a computational circuitry a number of tandem repeats with the variable number tandem repeat region for a set of sequenced copies of the plurality of copies, and determining with the computational circuitry based at least in part on determining the number of tandem repeats a statistical value indicative of the allele.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

The present disclosure relates to the field of genetic analysis, for example, the field of polynucleotide (e.g., DNA) analysis for the purpose of, for example, human identification, or the identification within or between other species of plants, animals or other living organisms.

Various embodiments relate to methods for typing one or a set of genetic markers that can be used to distinguish or identify humans. For example, in some embodiments, the method can utilize an array of sensors (e.g., a nanopore array, chemFET array, etc.) that simultaneously, in parallel, make measurements on a sample (e.g., genetic marker fragments) derived from a test subject or DNA sample, wherein each sensor obtains only partial or inaccurate data, but the results are aggregated across the output of the entire array to accurately infer the marker state of the sample. In some embodiments, the measurements are not taken simultaneously.

In some embodiments, such a sensor array (having any number of sensors) is further amenable to a very compact form, which can be deployed for field use in human identification. For example, systems and methods are provided in which data is acquired and analyzed locally at point-of-contact, routed back to a centralized database of known marker profiles, and information on whether the data corresponds to a profile of one or more individuals in the database can be returned to the point of contact. Further, in some embodiments, a system or process can be applied for identification outside of human identification, specifically in the case of identifying or distinguishing individuals from within another species in the field, such as cattle, or for distinguishing species in the field, such as insects.

Microsatellite genetic markers are DNA sequence elements in the genome of a particular species, in which a simple sequence unit (repeat unit) of a length k (e.g., k=3) repeats N times, and in which N is variable, or polymorphic, across individuals of that species. The microsatellite genetic markers can thus be used as a traceable marker to distinguish the DNA from different individuals within the species. Microsatellite markers are also interchangeably referred to as Short Tandem Repeat (STR) or Variable Nucleotide Tandem Repeat (VNTR) markers.

For example, the sequence S=GATGATGATGAT (SEQ. NO. 1) can be a microsatellite with repeat unit [GAT], which is a k=3 mer, and a repeat count of N=4. In other examples, the repeat unit can include at least two nucleotides, such as at least three nucleotides, at least four nucleotides, at least five nucleotides, or even at least six nucleotides. Typically, k is in the range of 2 to 5, such as in a range of 3 to 5. The microsatellite can include at least four repeat units (i.e., N≥4), such as at least six repeat units, or at least 10 repeat units. For example, N can be in the range of 10 to 30.

Figure 1:
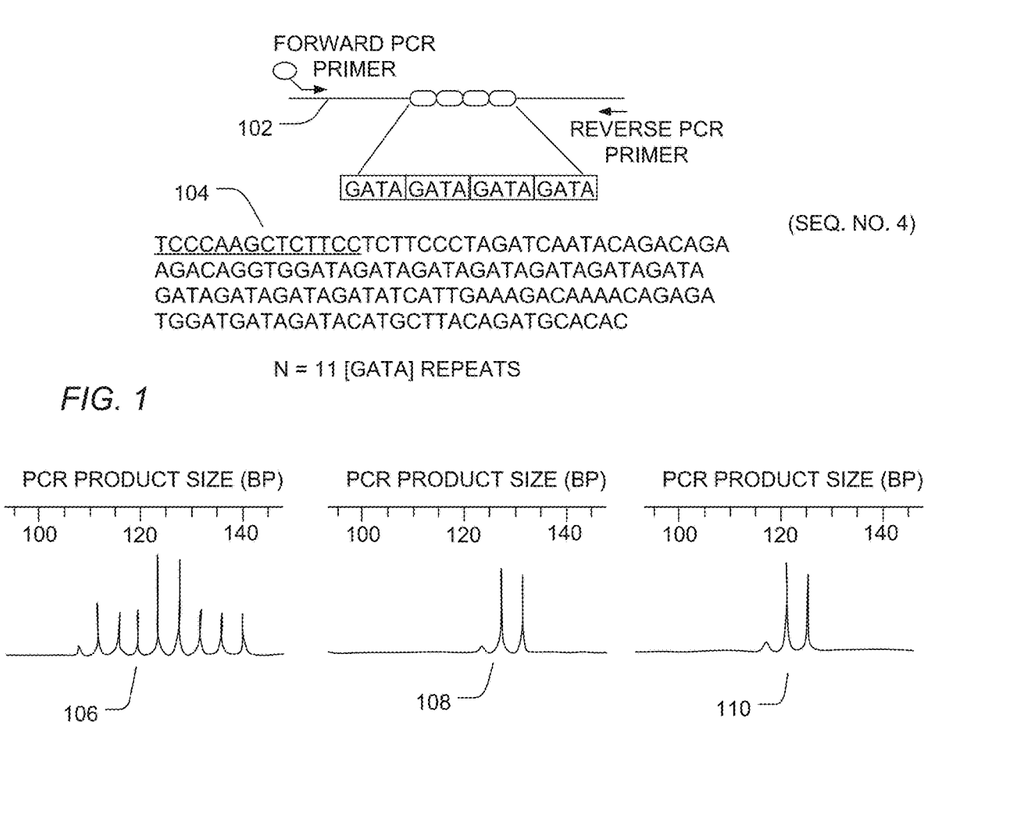
FIG. 1 illustrates a microsatellite or STR marker.

In a particular example, FIG. 1 includes an illustration of a microsatellite or STR marker. In the upper left of FIG. 1 illustrates how polymerase chain reaction (PCR) can be used to amplify the fragment 102 of interest. The lower left of FIG. 1 illustrates a conventional sequence 104 for a [GATA] repeat, with N=11 repeat units of size k=4. The right panel of FIG. 1 illustrates the genotypes of two individuals (108, 110), relative to a ladder 106 of the possible fragment sizes, as can be used in a standard gel sizing analysis.

A collection of several such markers in the genome can be used as a "DNA fingerprint" to reliably identify or distinguish individuals, for example, for criminal or forensic applications, or can be used to trace inheritance of portions of the genome that are passed from parent to child, for example, in the context of paternity testing or in performing genetic linkage studies that correlate inherited disease with inherited DNA fragments to isolate the causative genetic variants.

Figure 3:
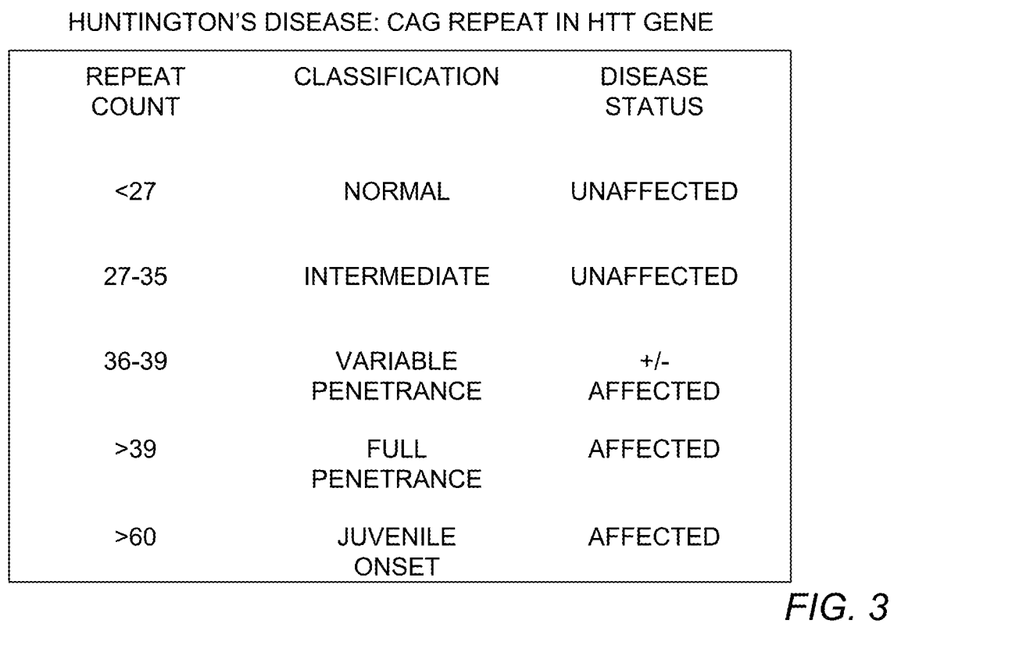
FIG. 3 illustrates an example of a disease caused by triplet repeats.

There are also cases of specific microsatellite repeats that appear within genes, in which the number of repeat units has functional implications and may be the difference between a disease or non-disease state. In particular, such functional implications occur in triplet repeat expansion disorders, such as Huntington's disease, where k=3 and the repeat units code for amino acids. An excessive number N of repeat units produces a long, dysfunctional protein resulting in disease. As illustrated in FIG. 3, the repeat causing Huntington's disease occurs within the coding part of the HTT gene. The number of repeat units alters the resulting protein. The repeat length is related to disease severity, as indicated, with lengths <27 being normal.

For a given microsatellite marker, the number of repeat units that occur in an individual is referred to as their genotype at that marker. In the case of diploid organisms, each marker in the autosome occurs as two alleles, and the genotype is a pair of numbers (N1, N2) that characterize the repeat numbers of the two alleles. Generally, the genotype numbers are the number of repeat units, but in current practice, the length of a PCR amplicon including the marker is used as a correlate. The two numbers refer to length of the PCR product resulting from that individual, (L1, L2), which is measured from the banding pattern that results when the amplicons are run on a electrophoresis size separation gel, in either slab or capillary format.

Typically, microsatellite markers have repeat unit lengths of at least two nucleotides, such as at least three nucleotides, at least four nucleotides, at least five nucleotides, or even at least six nucleotides. Typically, k is in the range of 2 to 6, such as in a range of 2 to 5 or a range of 2 to 4. The microsatellite can include at least four repeat units (i.e., N≥4), such as at least six repeat units, or at least 10 repeat units. The number (N) of repeat units typically varies between 5 and 30, such as between 10 and 30, although for each given microsatellite, typically only 4 to 10 different repeat states (N values) are observed in the population.

Figure 2:
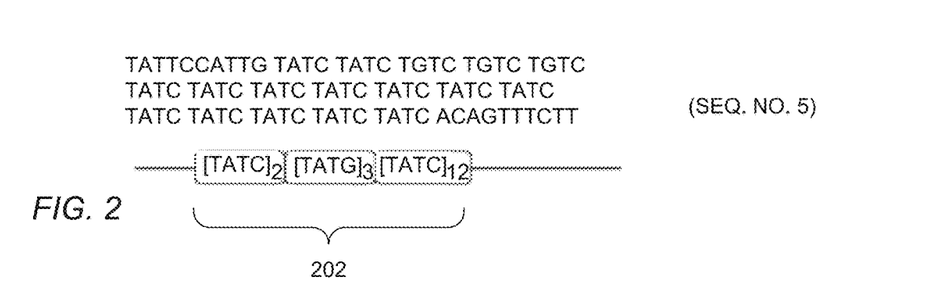
FIG. 2 illustrates an example of a microsatellite with an imperfect repeat structure.

The repeat unit may not be exactly repeated, rather there may be minor mutations to the repeat structure that have accrued over the course of evolution of the species in question. For example, a k=3, N=4 repeat that corresponds to GAAGAAGAAGAAGAA (SEQ. NO. 2) may occur in the species as GAAGAAGATGAAGAA (SEQ. NO. 3), wherein one of the A bases has mutated to a T in an ancient mutational event now fixed in the species. See FIG. 2 for a further example. Such imperfect repeats are still generally considered microsatellites and are of the same utility as polymorphic markers. FIG. 2 includes an illustration of an example of a microsatellite 202 with an imperfect repeat structure. The consensus repeat unit [TATC] co-occurs with units that are [TGTC].

Figure 4:
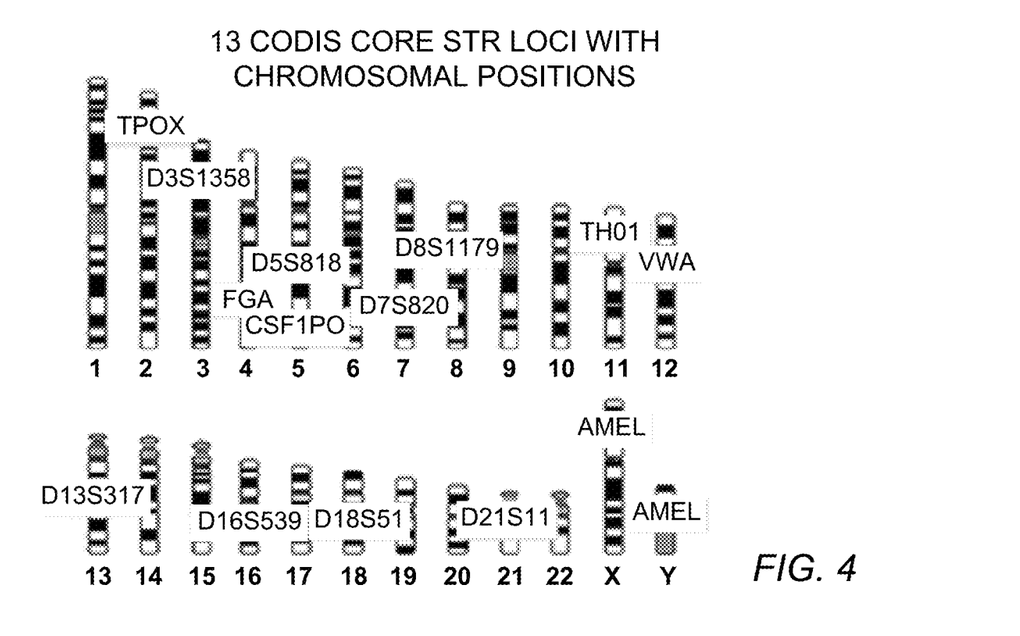
FIG. 4 illustrates an exemplary genome location of the 13 CODIS markers used by the Federal Bureau of Investigation for human identification.
Figure 5:
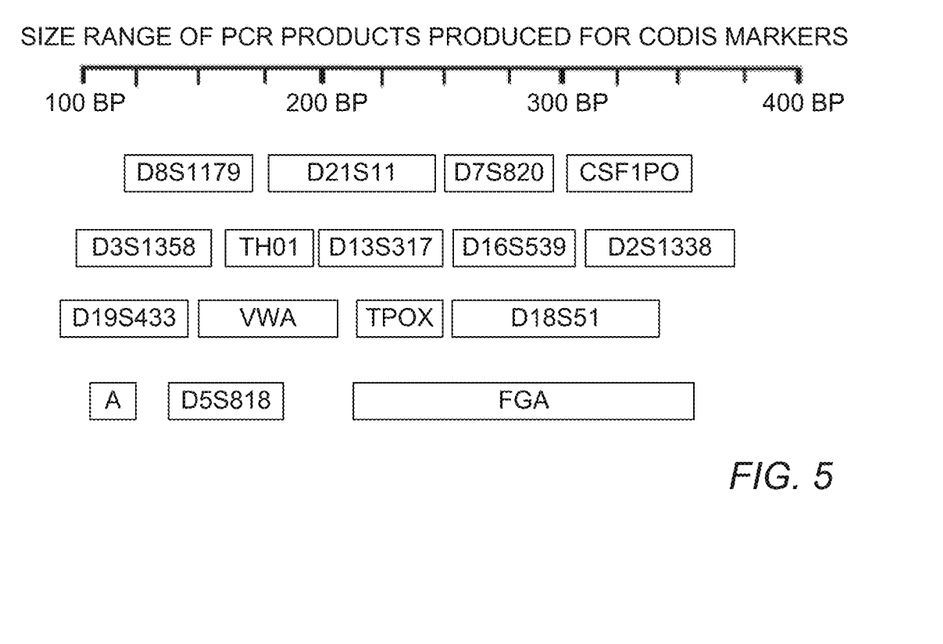
FIG. 5 illustrates size ranges of PCR products used to type the CODIS markers.

An example of a panel of markers widely used for Human Identification (HID) purposes is the Combined DNA Index System (CODIS) (see FIG. 4 and FIG. 5), which is the basis of the DNA fingerprint database used by the FBI in the United States. As illustrated in FIG. 4, CODIS consists of 13 different autosomal microsatellite markers with tetra nucleotide repeats (unit length k=4) and with N in the ranges of 10-30. FIG. 5 illustrates size ranges of PCR products used to type the CODIS markers. The fragments range from 100 bases to 400 bases in length. Each row indicates a different dye used to multiplex the gel sizing.

In addition, the CODIS system uses the AMEL marker to determine sex, which is a marker with alleles on the X and Y chromosomes. Such a marker is not a microsatellite, but instead differs by a 6-letter deletion on X, which allows distinction between the form on the X and Y-chromosomes, and thus allows distinction between XY (male) and XX (female) types. Even though AMEL is not a microsatellite, it can be typed using a form of the nanopore-based or FET-based techniques described here.

Other closely related sets are used for standardized HID in various other countries or regions, for example:

U.S. Core Loci (CODIS): CSF1PO, FGA, TH01, TPDX, VWA, D3S1358, D5S818, D7S820, D8S1179, D13S317, D16S539, D18S51, D21S11, AMEL Extended European Standard Set (ESS): FGA, TH01, VWA, D1S1656, D2S441, D3S1358, D8S1179, D10S1248, D12S391, D18S51, D21S11, D22S1045 Additional European Loci: D2S1338, D16S539, D19S433, SE33, AMEL UK Core Loci: FGA, TH01, VWA, D2S1338, D3S1358, D8S1179, D16S539, D18S51, D19S433, D21S11, AMEL German Core Loci: FGA, TH01, SE33, VWA, D3S1358, D8S1179, D18S51, D21S11, AMEL Interpol Standard Set of Loci: FGA, TH01, VWA, D3S1358, D8S1179, D18S51, D21S11; Optional: AMEL The problem of distinguishing individuals within a species, or distinguishing between species, can in general be solved using suitable DNA fragments as genetic markers, sufficiently diverse to distinguish individuals, or species. In the context of human identification, the current US standard used by the FBI, local law enforcement, and for paternity testing, is based on the CODIS set of genetic markers. This is a set of twelve tetra-repeat (4 base) Short Tandem Repeat (STR) markers that are highly variable in the number of repeat units between individuals, plus one 6 base deletion marker on the XY chromosomes, and which taken together as a "genetic fingerprint", suffice to uniquely identify most humans, aside from very rare circumstances. The same or similar marker sets, often including and slightly extending these, are used widely in other countries. It is also possible to create similar sets of markers based on STR or deletion fragments in other species to distinguished individuals within a species, such as for dogs. Also, to distinguish between species, it is possible to use several well known "Barcode of Life" markers, which are special DNA fragments present in most species, which have variable regions that distinguish species and strains. For example, to distinguish most animal species, a 648 base-pair region in the mitochondrial Cytochrome C Oxidase 1 gene ("CO1") can be used, in which there are several specific regions that vary, and the great majority of the rest remains unchanged.

Traditionally, these STR markers, and other markers that use fragment length as the principle difference, have been typed via Capillary Electrophoresis (CE) with optical detection on an instrument such as the Applied BioSystems 3730 DNA Analyzer. The same is true for BarCode of Life species identification applications, which typically rely on full Sanger Sequencing on such an instrument. Thus, traditionally, samples have been collected in the field and sent back to more centralized labs for processing.

In some embodiments, the present disclosure provides all-electronic sensor array chips, which fundamentally enable much smaller, more rapid and less expensive devices well suited for distributed field deployment and near-real time analysis and identification. The weakness of sensor array systems is that often each individual sensor does not produce the same quality of data as traditional CE optical systems, and thus cannot readily replace the older technology due to data quality concerns.

In some embodiments, the present disclosure utilizes a large number of sensors on an array. In some embodiments, each sensor (or at least some of the sensors) produces a read (e.g., any type of detectable signal) that is not itself of sufficient accuracy, but when suitably averaged together across many sensors, the genetic marker types can be reliably distinguished, giving the array-based approach a capability not inherent in the single or small number of sensors. This in turn can enable a point-of-contact, near-real time identification process in which markers of interest can be isolated from a genetic sample, via PCR or other capture methods, can be introduced to the sensor for highly redundant parallel reads, the parallel reads can be aggregated into those corresponding to the same genetic locus marker, and can then be further clustered and averaged to determine which marker states are present. In some embodiments, these states can then be queried against a remote database of marker profiles via an internet or wireless communications network, and returned to the point-of-use. In some embodiments, the data can indicate whether there are one or more possible matches in the database, and can determine the identity of those matches.

In some embodiments, the presently disclosed system and method can be utilized for human identification. For example, the system and method can be utilized with the CODIS markers, or other marker sets commonly used in Human Identification, as well as the cases of distinguishing species via BarCode of Life markers.

In some embodiments, a system is capable of performing high accuracy detection at the point of use, querying back to a central database or reporting this data (or data analysis) back to the point of use (or some other location) for rapid on-site identification (or any other desired use). In some embodiments, the present disclosure provides high accuracy marker fragment typing by properly averaging across many lower information fragment measurements from a sensor array. The sample can be a single molecule, a clonal template, or a mixture of clonal templates (such as two alleles form an individual amplified onto a bead or one local cluster). Various sensor arrays can be used. For example, the sensor array can be a nanopore array, a nanopore-ion-current sensor, a field effect transistor (FET) array, such as a chemFET sensor array, or any combination thereof.

In an example, DNA is extracted from a specimen or person. The DNA is fragmented and can be amplified to make copies of the fragments. The amplified genetic fragments can be applied to a sensor array so that more than one copy can be detected or measured by more than one sensor of the sensor array.

Figure 6:
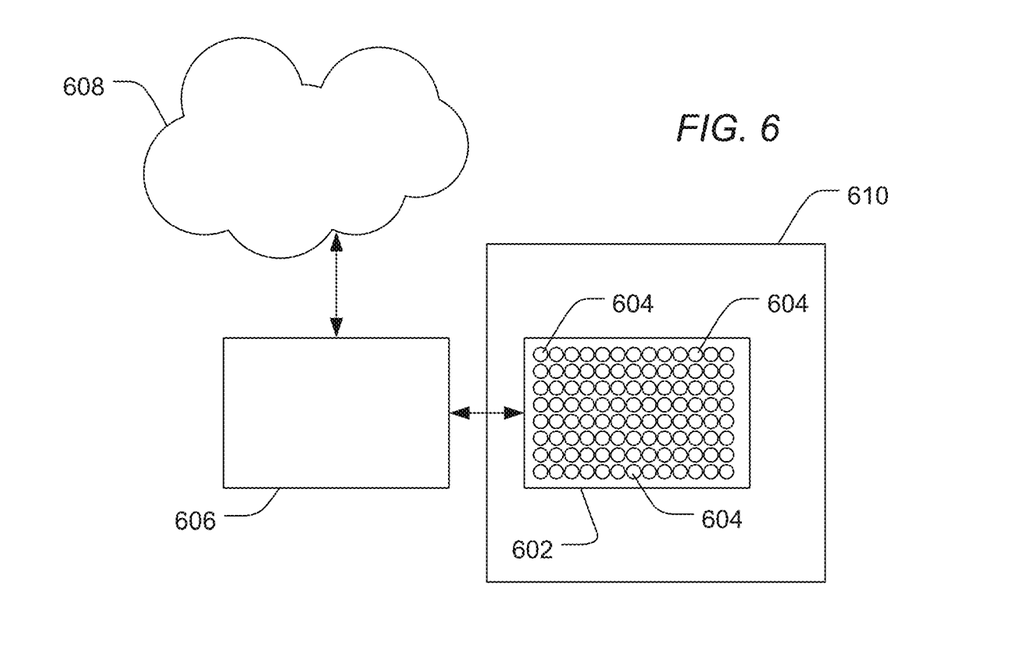
FIG. 6 includes an illustration of an exemplary system.

For example, as illustrated in FIG. 6, a sensor array 602 includes sensors 604. Signals generated when fragments of DNA are applied to the sensors 604 are transmitted from the sensor array 602 to a computational device 606. Optionally, the computational device can analyze the signal to determine characteristics of the copies of the genetic fragments. Alternatively, the computational device 606 can pass the signals to remote servers or to cloud-based applications 608 that can perform the analysis remotely and return data to the computational circuitry 606. Once characteristics of copies of the DNA fragments are measured, the measured characteristics can be aggregated and a statistical value indicative of an allele associated with the region located on the copies of the DNA fragments can be determined. In particular, the statistical value can be an average, such as mean, median, or mode of the measured characteristics. For example, the measuring the characteristic can include determining a number of repeats within a variable number tandem repeat region of a DNA fragment. Because rapid sequencing systems can provide lower accuracy measurement, sequence data is analyzed to determine a number of repeat units identified by the individual sensors. The repeat data is aggregated and a mean or mode value is determined. The mean or mode value may indicate the most likely allele type associated with the repeat region of the DNA fragment. In an example, the most likely allele is selected for comparison to data within a database. In another example, a search can be expanded to include a second most likely allele to provide a list of candidates.

The array 602 can include sensors 604 of various sensor types. For example, the sensors 604 can include nanopores or can be FET-based sequencing sensors. The sensor array 602 can reside within a container 610. When the sensor array includes a nanopore, the sensor array 602 can separate the container 610 into two compartments so that DNA fragments pass through the sensor array 602 between compartments. When a FET-based sequencing system is used, the sensor array can reside at a wall of the container 610 and wells of the array can be in fluid communication with fluid passing through the container 610.

A nanopore sensor is a small, nanometer-scale channel, hole or "pore" passing through a physical barrier otherwise impermeable to ions. In particular embodiments, when the pore is in contact with an ionic solution and placed under a suitable applied voltage, a measureable ion current flows. When the pore or channel is partially obstructed by the presence of another molecule, the current is altered. In this way, the sensor can be used to make measurements on molecules that block or pass through the pore, particularly those that carry a charge in solution and are thus driven into or through the pore by the applied voltage. In another embodiment, the presence of particular molecules, such as nucleotides of a nucleic acid strand cause a change in the nanopore, such as a change in conductance within a semiconductor region or a change in conductance through the fluid within the pore, that results in a signal characteristic of the nucleotides of the strand. Nanopores of the nanopore sensors can have an opening having a diameter in a range of 1 nm to 10 nm. For devices having an opening in the size range of 1 nm to 3 nm, double-stranded DNA can be excluded.

In particular, in the context of measuring DNA, the DNA strand may be induced to pass through a nanopore, and there can be differential current signals for single stranded DNA, double stranded DNA, for different adducts bound to such DNA, and even due to the base composition of the DNA itself. The nanopore can be a porin protein, such as Alpha Hemolysin (aHL), or MspA, either in their native or mutant forms, embedded in a lipid bilayer (See FIG. 10), or can be a fabricated hole created in a solid state membrane using techniques from lithography and semiconductor manufacturing, such as e-beam lithography, photolithography, or chemical vapor deposition. In an example, the nanopore can be structured as a passive circuit including two electrodes. In another example, the nanopore can be structured as an active circuit, such as an FET device including a source, drain, and gate material.

Figure 7:
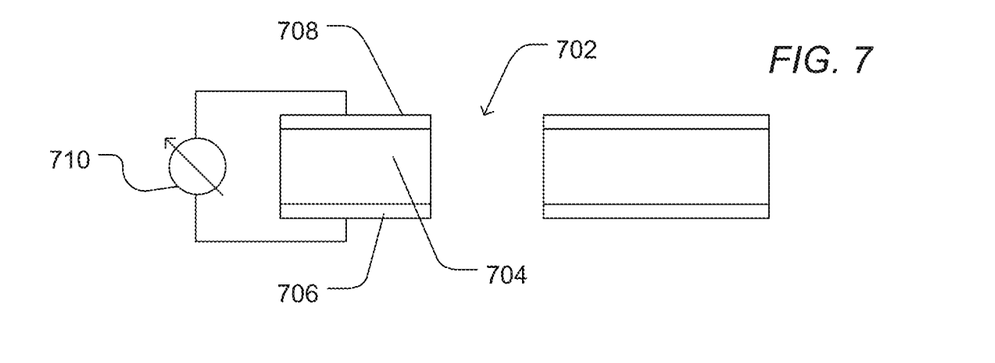
FIG. 7, FIG. 8, FIG. 9, and FIG. 10 include a cross sectional views of an exemplary nanopore devices.

FIG. 7 includes an illustration of an exemplary system that includes a nanopore 702 defined in an insulator material 704. Electrodes 706 or 708 can be positioned on opposite sides of the nanopore 702. An electrical potential between the electrodes 706 and 708 can be measured at 710 to determine ion flow through the nanopore 702. When a DNA fragment passes through the nanopore 702, ion current can be restricted and the amount of ion current can be correlated with sequence of nucleotides within the DNA fragment.

Figure 8:
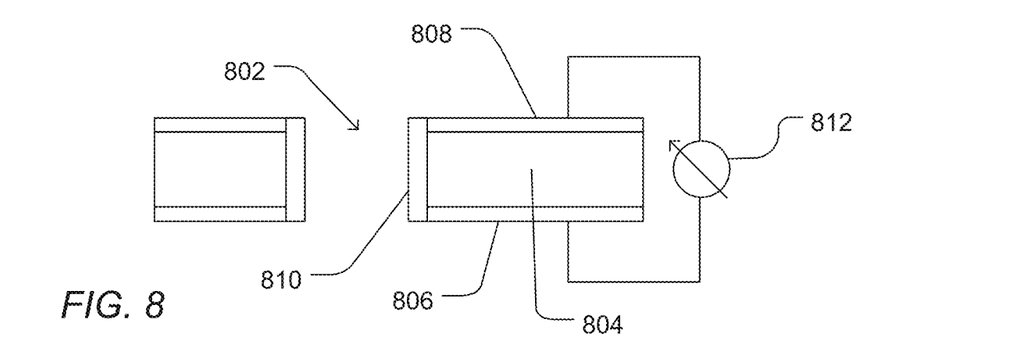

In another example, a nanopore 802 as illustrated in FIG. 8 is formed in a semiconductor material 804. The semiconductor material 804 is isolated from the nanopore 802 by an insulator 810. Source and drain regions 806 or 808 are disposed on opposite sides of the semiconductor material 804. The source and drain regions 806 or 808 can be isolated from solutions by other layers (not illustrated). When DNA passes through the nanopore 802, bases within the polynucleotide cause different changes in resistance or conductance within the semiconductor material 804. The changes in resistance or conductance can be measured at 812 based on voltage or on current flowing between the source and drain 806 or 808.

Figure 9:
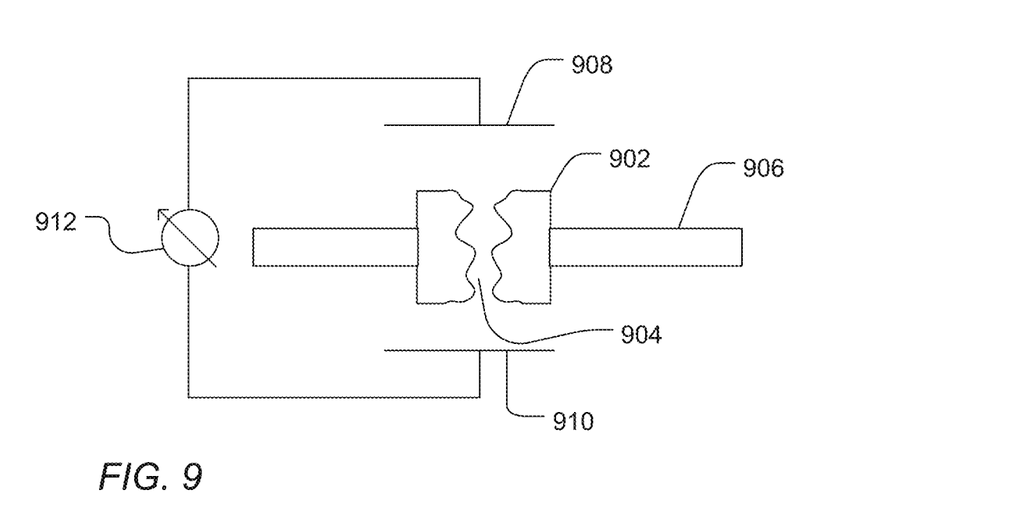

In a further example illustrated in FIG. 9, a protein 902 defines a nanopore 904 within an impermeable membrane 906, such as a lipid bilayer. Electrodes 908 and 910 disposed on opposite sides of the nanopore 904 can detect the change in ion current at 912. When a DNA fragment passes through the protein nanopore 902 a change in ion current is measured at 912, which can be indicative of the nucleotide bases passing through the nanopore.

Figure 10:
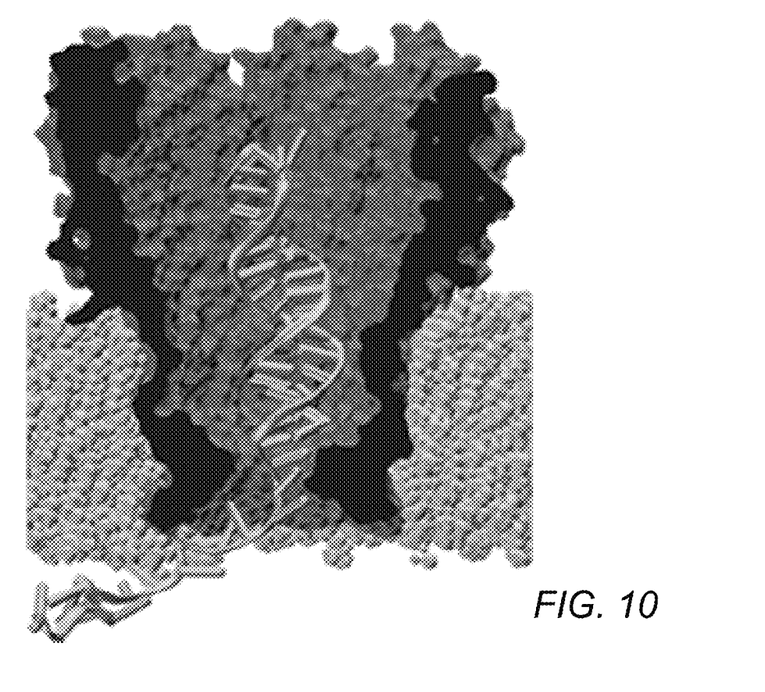

FIG. 10 includes an illustration of a cross-sectional view of a protein nanopore (MspA) containing a strand of single stranded DNA, whose motion through the channel has been blocked by the binding of a complementary DNA binding probe (double stranded region). The ion current through the pore is reduced by the double strand.

In another example, the array can be an array of sensors including a field effect transistor (FET) associated with a well. DNA fragments can be secured within the well using a polymer matrix, a polymeric particle, or by direct coupling to a surface of the well.

Figure 11:
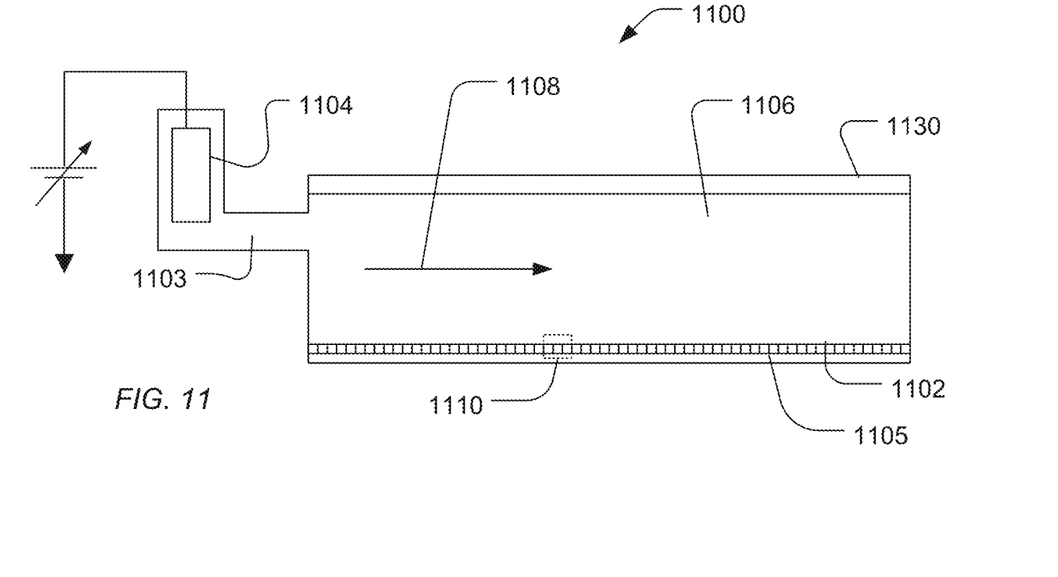
FIG. 11 and FIG. 12 include illustrations of exemplary transistor-based systems.

In a particular embodiment, a sequencing system includes a flow cell in which a sensory array is disposed, includes communication circuitry in electronic communication with the sensory array, and includes containers and fluid controls in fluidic communication with the flow cell. In an example, FIG. 11 illustrates an expanded and cross-sectional view of a flow cell 1100 and illustrates a portion of a flow chamber 1106. A reagent flow 1108 flows across a surface of a well array 1102, in which the reagent flow 1108 flows over the open ends of wells of the well array 1102. The well array 1102 and a sensor array 1105 together can form an integrated unit forming a lower wall (or floor) of flow cell 1100. A reference electrode 1104 can be fluidically coupled to flow chamber 1106. Further, a flow cell cover 1130 encapsulates flow chamber 1106 to contain reagent flow 1108 within a confined region.

Figure 12:
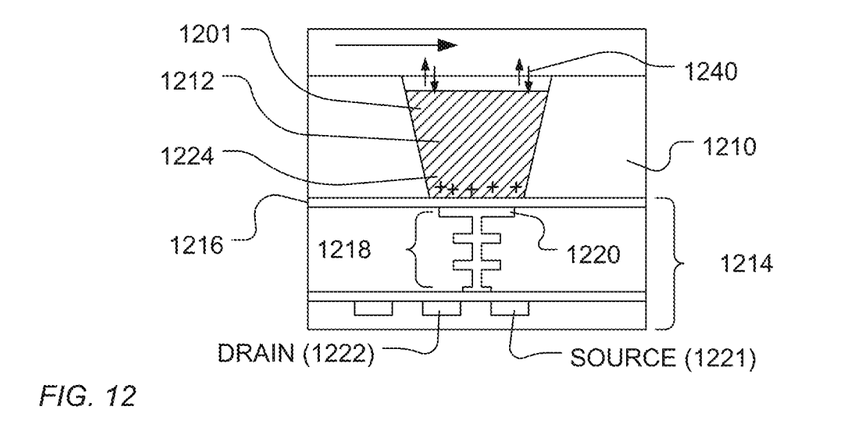

FIG. 12 illustrates an expanded view of a well 1201 and a sensor 1214, as illustrated at 1110 of FIG. 11. The volume, shape, aspect ratio (such as base width-to-well depth ratio), and other dimensional characteristics of the wells can be selected based on the nature of the reaction taking place, as well as the reagents, byproducts, or labeling techniques (if any) that are employed. The sensor 1214 can be a chemical field-effect transistor (chemFET), more specifically an ion-sensitive FET (ISFET), with a floating gate 1218 having a sensor plate 1220 optionally separated from the well interior by a material layer 1216. In addition, a conductive layer (not illustrated) can be disposed over the sensor plate 1220. In an example, the material layer 1216 includes an ion sensitive material layer. The material layer 1216 can be a ceramic layer, such as an oxide of zirconium, hafnium, tantalum, aluminum, or titanium, among others, or a nitride of titanium. In an example, the material layer 1216 can have a thickness in a range of 5 nm to 100 nm, such as a range of 10 nm to 70 nm, a range of 15 nm to 65 nm, or even a range of 20 nm to 50 nm.

While the material layer 1216 is illustrated as extending beyond the bounds of the illustrated FET component, the material layer 1216 can extend along the bottom of the well 1201 and optionally along the walls of the well 1201. The sensor 1214 can be responsive to (and generate an output signal related to) the amount of a charge 1224 present on material layer 1216 opposite the sensor plate 1220. Changes in the charge 1224 can cause changes in a current between a source 1221 and a drain 1222 of the chemFET. In turn, the chemFET can be used directly to provide a current-based output signal or indirectly with additional circuitry to provide a voltage-based output signal. Reactants, wash solutions, and other reagents can move in and out of the wells by a diffusion mechanism 1240.

In an embodiment, reactions carried out in the well 1201 can be analytical reactions to identify or determine characteristics or properties of an analyte of interest. Such reactions can generate directly or indirectly byproducts that affect the amount of charge adjacent to the sensor plate 1220. If such byproducts are produced in small amounts or rapidly decay or react with other constituents, multiple copies of the same analyte can be analyzed in the well 1201 at the same time in order to increase the output signal generated. In an embodiment, multiple copies of an analyte can be attached to a solid phase support 1212, either before or after deposition into the well 1201. The solid phase support 1212 can be a polymer matrix, such as a hydrophilic polymer matrix, for example, a hydrogel matrix or the like. Alternatively, the solid phase support 1212 can include a polymeric particle. In another alternative, fragments can be coupled directly to a surface of the well 1201.

The well 1201 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 1201 can have a characteristic diameter, defined as the square root of 4 times the cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 1201 can have a characteristic diameter of at least 0.01 micrometers.

Figure 14:
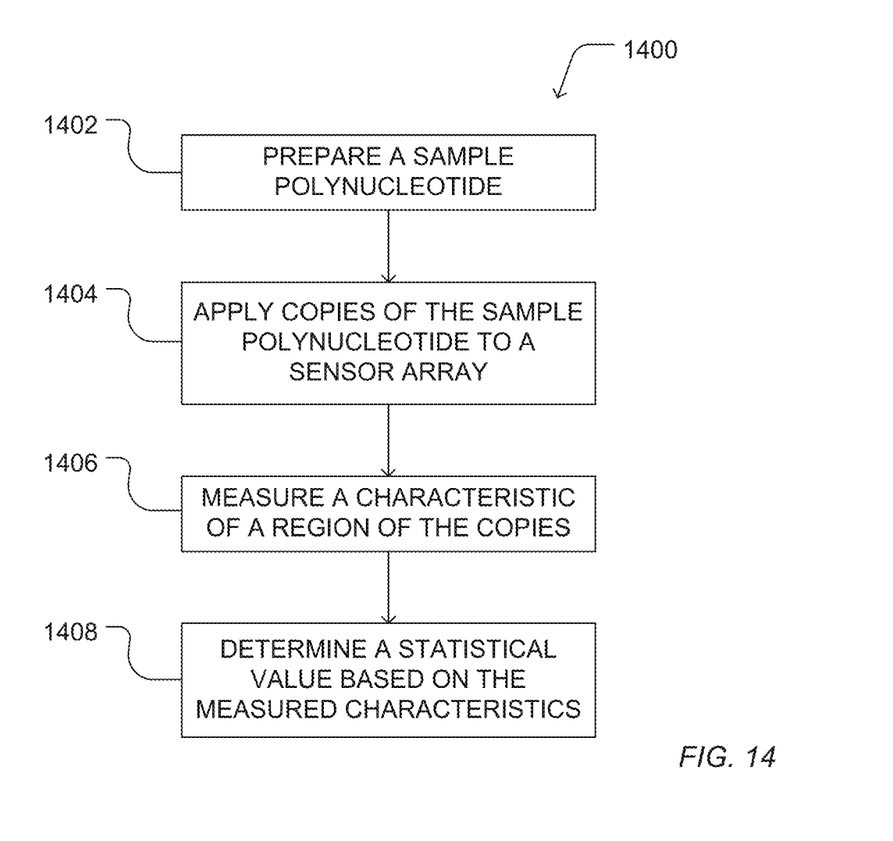
FIG. 14 includes a flow diagram of an exemplary method.

As illustrated in FIG. 14, a method 1400 includes preparing a sample polynucleotide, as illustrated at 1402. In an example, preparing the sample polynucleotide can include extracting DNA from a specimen or human individual. The DNA can be fragmented and fragments of interest can be amplified to form copies of the fragments. In particular, the fragments of interest can include regions indicative of alleles, such as variable number tandem repeat regions.

The amplified copies of the sample polynucleotide can be applied to a sensor array, as illustrated at 1404. For example, sensor array can include a nanopore sensor array or a field effect transistor (FET) based sensor array. In an example, the copies of the sample polynucleotide can be applied to pass through the nanopores. In another example, copies of the polynucleotide can be applied to wells overlying a FET sensor array and can be sequenced by sequentially flowing polynucleotides over the sequencing array and measuring the response to the polynucleotides with the FET sensors.

Sensors of the sensor array can measure a sequence or a characteristic of the region of the copies of the sample polynucleotide, as illustrated at 1406. Different copies may be applied through different sensors. In another example, more than one copy can be applied to a single sensor of the array. Each measurement is analyzed to determine a characteristic of the region.

Figure 13:
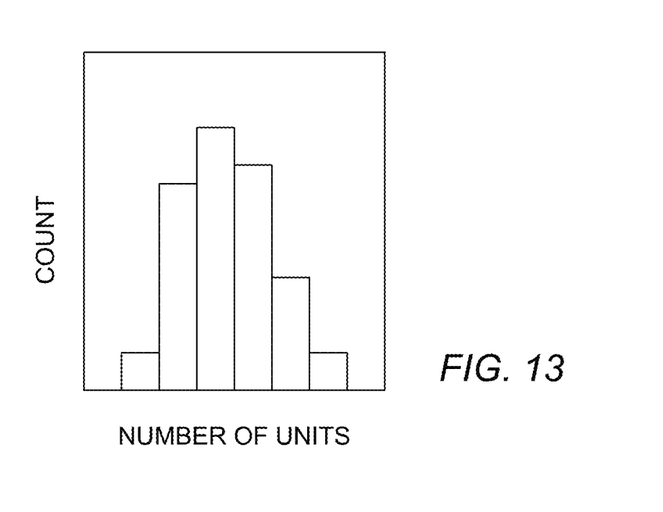
FIG. 13 includes an illustration of exemplary data.

Data associated with the measurement is aggregated and a statistical value is determined based at least in part on the measured characteristics, as illustrated at 1408. The data can be aggregated, as illustrated in FIG. 13 to provide a distribution of measured values. The statistical value can be determined based on a distribution, as illustrated in FIG. 13. The statistical value can include determining an average. In an example, the statistical value is a mean. In another example, the statistical value is a mode. In a further example, the statistical value is a median.

The mean, mode, or median value can be used to select an allele, which can be compared to data within a database to determine a candidate. In another example, a second allele can be selected as an alternative based on the mean, mode, or median value to identify a list of potential matches.

In a first aspect, a method of genotyping includes applying a sample solution including a plurality of copies of a sample polynucleotide to an array of sensors. The sample polynucleotide includes a region associated with an allele. The method further includes measuring using a plurality of sensors of the array of sensors a characteristic of the region of the plurality of copies of the sample polynucleotide and determining using a computational circuitry and the measured characteristics a statistical value indicative of the allele.

In an example of the first aspect, the allele is associated with human identification.

In another example of the first aspect and the above examples, the array of sensors includes an array of ion sensitive field effect transistors.

In a further example of the first aspect and the above examples, the array of sensors includes an array of protein nanopores, each associated with an electrode.

In an additional example of the first aspect and the above examples, the array of sensors includes an array of semiconductor nanopores.

In another example of the first aspect and the above examples, the region is a variable number tandem repeat region and the characteristic includes a number of tandem repeats. For example, determining the statistical value includes determining a mean number of tandem repeats. In another example, determining the statistical value includes determining a mode number of tandem repeats.

In a further example of the first aspect and the above examples, the method further includes amplifying the sample polynucleotide to provide the plurality of copies of the sample polynucleotide.

In a second aspect, a method of genotyping includes applying a sample solution including a plurality of copies of a sample polynucleotide to an array of sensors. The sample polynucleotide includes a variable number tandem repeat region associated with an allele. The method further includes sequencing with a plurality of sensors of the array of sensors at least the variable number tandem repeat region of the plurality of copies of the sample polynucleotide, determining with a computational circuitry a number of tandem repeats with the variable number tandem repeat region for a set of sequenced copies of the plurality of copies, and determining with the computational circuitry based at least in part on determining the number of tandem repeats a statistical value indicative of the allele.

In an example of the second aspect, the allele is associated with human identification.

In another example of the second aspect and the above examples, the array of sensors includes an array of ion sensitive field effect transistors.

In a further example of the second aspect and the above examples, the array of sensors includes an array of protein nanopores, each associated with an electrode.

In an additional example of the second aspect and the above examples, the array of sensors includes an array of semiconductor nanopores.

In another example of the second aspect and the above examples, determining the statistical value includes determining a mean number of tandem repeats.

In a further example of the second aspect and the above examples, determining the statistical value includes determining a mode number of tandem repeats.

In an additional example of the second aspect and the above examples, the method further includes amplifying the sample polynucleotide to provide the plurality of copies of the sample polynucleotide.

In a third aspect, a method of genotyping includes amplifying a sample polynucleotide to provide a plurality of copies of the sample polynucleotide. The sample polynucleotide includes a variable number tandem repeat region associated with an allele associated with human identification. The method further includes applying a sample solution including the plurality of copies of a sample polynucleotide to an array of sensors, sequencing with a plurality of sensors of the array of sensors at least the variable number tandem repeat region of the plurality of copies of the sample polynucleotide, determining with a computational circuitry a number of tandem repeats with the variable number tandem repeat region for a set of sequenced copies of the plurality of copies, and determining with the computational circuitry based at least in part on determining the number of tandem repeats a statistical value indicative of the allele.

In an example of the third aspect, determining the statistical value includes determining a mean number of tandem repeats. In another example of the third aspect, determining the statistical value includes determining a mode number of tandem repeats.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of genotyping, the method comprising:
fragmenting DNA to form a plurality of fragments, the plurality of fragments including a sample polynucleotide including a variable number tandem repeat region associated with an allele of an individual;
amplifying at least the sample polynucleotide to form a sample solution including a plurality of copies of the sample polynucleotide;
applying the sample solution including a plurality of copies of a sample polynucleotide to an array of sensors having a corresponding well array, the sensors of the array of sensors including ion sensitive field effect transistors, copies of the plurality of copies being secured to polymer matrices in different wells of the well array associated with a plurality of sensors of the array of sensors;
sequencing with each sensor of the plurality of sensors of the array of sensors at least the variable number tandem repeat region of a copy of the plurality of copies of the sample polynucleotide, the ion sensitive field effect transistors providing current or voltage signals in response to sequencing reactions;
for the each sensor of the plurality of the sensors, determining with a computational circuitry, based on the current or voltage signals, a number of tandem repeats with the variable number tandem repeat region for a set of sequenced copies of the plurality of copies;
using the computational circuitry, aggregating from each sensor of the plurality of sensors the number of tandem repeats;
determining with the computational circuitry based at least in part on aggregating the number of tandem repeats an average value of a tandem repeat; and
identifying the individual based in part on the average value of the tandem repeat.

2. The method of claim 1, wherein the allele is associated with human identification.

3. The method of claim 1, wherein determining the average value includes determining a mean number of tandem repeats.

4. The method of claim 1, wherein determining the average value includes determining a mode number of tandem repeats.

5. A method of genotyping, the method comprising:
fragmenting DNA to form a plurality of fragments, the plurality of fragments including a sample polynucleotide, the sample polynucleotide having a variable number tandem repeat region associated with an allele associated with human identification of an individual;
amplifying a sample polynucleotide to provide a sample solution including a plurality of copies of the sample polynucleotide;
applying the sample solution including the plurality of copies of a sample polynucleotide to an array of sensors having a corresponding well array, the sensors of the array of sensors including ion sensitive field effect transistors, copies of the plurality of copies being secured to polymer matrices in different wells of the well array associated with a plurality of sensors of the array of sensors;
sequencing with each sensor of the plurality of sensors of the array of sensors at least the variable number tandem repeat region of a copy of the plurality of copies of the sample polynucleotide;
for each sensor, determining with a computational circuitry a number of tandem repeats with the variable number tandem repeat region for the copy of the plurality of copies;
aggregating from each sensor of the plurality of sensors the number of tandem repeats to form a distribution;
determining with the computational circuitry based at least in part on aggregating the number of tandem repeats an average value of a tandem repeat; and
identifying the individual based in part on the average value of the tandem repeat.

6. The method of claim 5, wherein determining the average value includes determining a mean number of tandem repeats.

7. The method of claim 5, wherein determining the average value includes determining a mode number of tandem repeats.

* * * * *